United States Patent

Cohen et al.

[11] Patent Number: 4,650,812
[45] Date of Patent: Mar. 17, 1987

[54] 4-OXO-3,4-DIHYDRO-2H-1-BENZOPYRANYLOXY ALKANOIC ACID DERIVATIVES

[75] Inventors: Noal Cohen, Montclair; Guiseppe F. Weber, Cedar Grove, both of N.J.

[73] Assignee: Hoffmann-La Roche Inc., Nutley, N.J.

[21] Appl. No.: 692,479

[22] Filed: Jan. 18, 1985

Related U.S. Application Data

[63] Continuation-in-part of Ser. No. 674,193, Jan. 18, 1985, abandoned.

[51] Int. Cl.⁴ .................... C07D 311/22; A61K 31/35
[52] U.S. Cl. ...................................... 514/456; 549/401
[58] Field of Search ........................ 549/401; 514/456

[56] References Cited

U.S. PATENT DOCUMENTS 4,546,194 10/1985 Miyano et al. ...................... 549/401

FOREIGN PATENT DOCUMENTS 61800 10/1982 European Pat. Off. .
79637 5/1983 European Pat. Off. .
2237100 7/1972 Fed. Rep. of Germany .

OTHER PUBLICATIONS

Derwent 83-706997/28.
Derwent 83-700027/42.
Derwent 27835 D/16 (1981).
Derwent 61843 E/80 (1981).
C.A. 98-89158b (1983).

Primary Examiner—Nicky Chan
Attorney, Agent, or Firm—Jon S. Saxe; Bernard S. Leon; William G. Isgro

[57] ABSTRACT

The invention relates to compounds of the formula

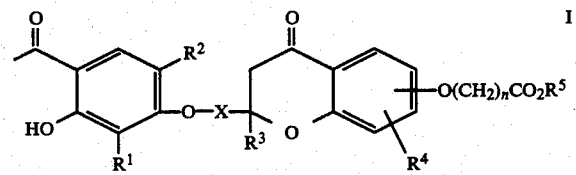

wherein $R^1$ is hydrogen or lower alkyl, $R^2$ is hydrogen or halogen, $R^3$ is hydrogen or lower alkyl, $R^4$ is hydrogen or lower alkyl, $R^5$ is hydrogen, lower alkyl or aralkyl, X is alkylene and n is an integer from 1 to 6, enantiomers thereof, and, when $R^5$ is hydrogen, salts thereof with pharmaceutically acceptable bases.

18 Claims, No Drawings

4-OXO-3,4-DIHYDRO-2H-1-BENZOPYRANYLOXY ALKANOIC ACID DERIVATIVES

CROSS REFERENCE TO RELATED APPLICATIONS

This application is a continuation-in-part of U.S. application Ser. No. 674,193, filed Jan. 18, 1985, now abandoned.

BRIEF SUMMARY OF THE INVENTION

The invention relates to compounds of the formula

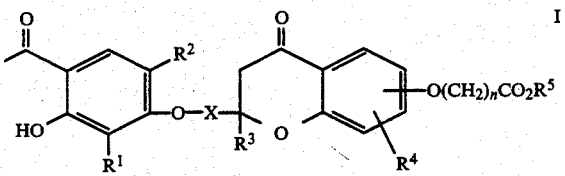

wherein $R^1$ is hydrogen or lower alkyl, $R^2$ is hydrogen or halogen, $R^3$ is hydrogen or lower alkyl, $R^4$ is hydrogen or lower alkyl, $R^5$ is hydrogen, lower alkyl or aralkyl, X is alkylene and n is an integer from 2 to 6.

enantiomers thereof, and, when $R^5$ is hydrogen, salts thereof with pharmaceutically acceptable bases.

The compounds of formula I are useful as agents for the treatment of allergic conditions.

DETAILED DESCRIPTION OF THE INVENTION

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "halogen" or "HAL" denotes all the halogens, that is, bromine, chlorine, fluorine and iodine. The term "alkylene" denotes a straight or branched chain radical of 3 to 7 carbon atoms, for example, propylene, 2-methylpropylene, butylene, pentamethylene, hexamethylene, heptamethylene and the like. The term "aralkyl" denotes a straight or branched chain lower alkyl group in which one or more of the hydrogen atoms have been replaced by an aryl group, for example, benzyl and the like.

The invention relates to compounds of the formula

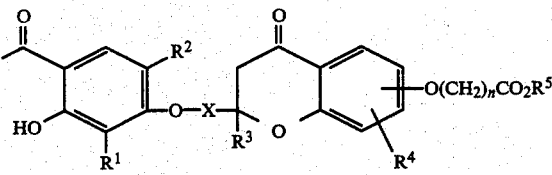

wherein $R^1$ is hydrogen or lower alkyl, $R^2$ is hydrogen or halogen, $R^3$ is hydrogen or lower alkyl, $R^4$ is hydrogen or lower alkyl, $R^5$ is hydrogen, lower alkyl or aralkyl, x is alkylene, and n is an integer from 1 to 6.

enantiomers thereof, and, when $R^5$ is hydrogen, salts thereof with pharmaceutically acceptable bases.

A preferred group of compounds of the invention are those of formula I in which $R^1$ is lower alkyl; $R^2$ is hydrogen; $R^3$ is lower alkyl; $R^4$ is lower alkyl; $R^5$ hydrogen or lower alkyl; X is alkylene of 4 to 6 carbon atoms; and n is 1 to 4.

A more preferred group of compounds of the invention are those of formula I in which $R^1$ is propyl; $R^2$ is hydrogen; $R^3$ is methyl; $R^4$ is propyl; $R^5$ is hydrogen or lower alkyl; X is alkylene of 4 to 6 carbon atoms; and n is 1 to 4.

Preferred compounds of formula I are:
rac-[[2-[6-(4-acetyl-3-hydroxy-2-propylphenoxy)hexyl]-3,4-dihydro-2-methyl-4-oxo-8-propyl-2H-1-benzopyran-7-yl]oxy]acetic acid; and rac-[[2-[4-(4-acetyl-3-hydroxy-2-propylphenoxy)butyl]-3,4-dihydro-2-methyl-4-oxo-2H-1-benzopyran-7-yl]oxy]acetic acid methyl ester.

Exemplary of the compounds of formula I are:
(R)-[[2-[4-(4-acetyl-3-hydroxy-2-propylphenoxy)butyl]-3,4-dihydro-2-methyl-4-oxo-2H-1-benzopyran-7-yl]oxy]acetic acid methyl ester;

(S)-[[2-[4-(4-acetyl-3-hydroxy-2-propylphenoxy)butyl]-3,4-dihydro-2-methyl-4-oxo-2H-1-benzopyran-7-yl]oxy]acetic acid methyl ester;

rac.-[[2-[4-(4-acetyl-3-hydroxy-2-propylphenoxy)butyl]-3,4-dihydro-2-methyl-8-propyl-4-oxo-2H-1-benzopyran-6-yl]oxy]acetic acid butyl ester;

rac.-6-[[2-[4-(4-acetyl-3-hydroxy-2-propylphenoxy)butyl]-3,4-dihydro-8-propyl-4-oxo-2H-1-benzopyran-7-yl]oxy]hexanoic acid;

rac.-5-[[2-[6-(4-acetyl-3-hydroxy-2-propylphenoxy)hexyl]-3,4-dihydro-2-methyl-8-propyl-4-oxo-2H-1-benzopyran-5-yl]oxy]pentanoic acid 2-methyl-1-butyl ester;

rac.-4-[[2-[8-(4-acetyl-3-hydroxy-2-propylphenoxy)octyl]-3,4-dihydro-2-ethyl-4-oxo-2H-1-benzopyran-6-yl]oxy]butanoic acid; and the like.

The compounds of formula I of the invention can be prepared as hereinafter described in Reaction Scheme I which follows.

Reaction Scheme I

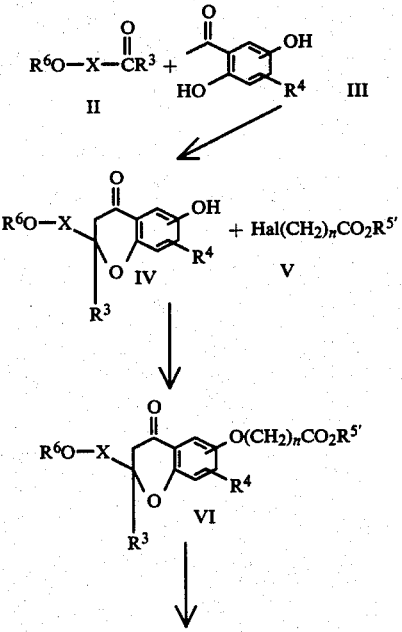

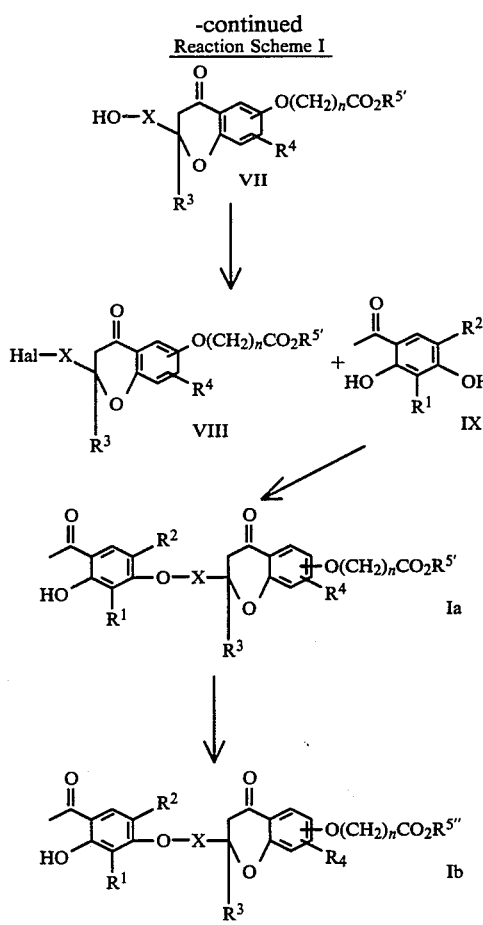

-continued
Reaction Scheme I wherein X, $R^1$, $R^2$, $R^3$, $R^4$, and n are as previously described, $R^{5'}$ is lower alkyl, $R^{5''}$ is hydrogen, $R^6$ is lower alkyl, and HAL is halogen.

In Reaction Scheme I, a compound of formula III, which are known compounds or can be prepared according to known procedures, is reacted with a compound of formula II, which are known compounds or can be prepared according to known procedures, to yield a compound of formula IV in the presence of a catalyst, for example, a cyclic secondary amine such as pyrrolidine, and a inert aromatic hydrocarbon, preferably toluene, at a temperature in the range of about 25° C. to about 150° C., preferably at about 110° C. The resulting compound of formula IV can be recovered utilizing conventional methods.

The reaction of a compound of formula V, which are known compounds or can be prepared according to known procedures, with a compound of formula IV to yield a compound of formula VI is carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of from about 70° to about 100° C., and in the presence of an acid acceptor, for example, potassium carbonate or the like. The preferred solvent is a mixture of acetone and dimethylformamide. The resulting compound of formula VI can be recovered utilizing conventional methods, for example, crystallization, chromatography or the like.

A compound of formula VI is converted to a compound of formula VIII utilizing as a catalyst a strong mineral acid such as dilute hydrochloric acid, sulfuric acid or an aryl- or alkylsulfonic acid such as para-toluenesulfonic acid, or the like, preferably dilute aqueous hydrochloric acid, in an organic solvent which is miscible with water such as acetone, methanol, ethanol, tetrahydrofuran, acetic acid or the like, preferably methanol, at a temperature in the range of from about 20° C. to about 150° C., preferably at 25° C.

A compound of formula VII is reacted with a sulfonyl chloride of the formula $R^7$ $SO_2Cl$, wherein $R^7$ is alkyl or aryl, such as phenyl, to yield a sulfonate utilizing conditions conventionally used for converting an alcohol to a sulfonate ester. The methansulfonate ester is preferred. For example, the sulfonation is carried out in an inert solvent, such as dichloromethane utilizing a sulfonating agent such as alkylsulfonyl chloride, preferably methanesulfonyl chloride in the presence of a base, for example, tri-lower alkylamine, pyridine or the like, preferably triethylamine, at a temperature in the range of from about 0° C. to about 25° C., preferably at 0° C. The resulting sulfonate ester can be recovered utilizing conventional methods. The sulfonate ester is converted to a compound of formula VIII utilizing conditions conventionally used for transforming a sulfonate ester to an alkyl halide. For example, the sulfonate ester is treated with an alkali metal halide for example, sodium iodide, lithium iodide, potassium iodide and the like, preferably sodium iodide, in a solvent, for example, a dialkyl ketone, such as ethyl methyl ketone, acetone and the like, preferably acetone, at a temperature in the range of from about 20° C. to about 100° C., preferably at 20° C. The resulting compound of formula VIII can be recovered utilizing conventional methods.

The reaction of a compound of formula IX, which are known compounds or can be prepared according to known procedures, with a compound of formula VIII to yield a compound of formula Ia is carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of from about 70° to about 100° C., and in the presence of an acid acceptor, for example, potassium carbonate or the like. The preferred solvent is a mixture of acetone and dimethylformamide. The resulting compound of formula Ia can be recovered utilizing conventional methods, for example, crystallization, chromatography or the like.

A compound of formula Ia can be converted to a compound of formula Ib by hydrolysis which is carried out with an alkali metal hydroxide, for example, lithium hydroxide, sodium hydroxide, potassium hydroxide or the like, in a mixture of water and a water miscible solvent, for example, methanol, ethanol, tetrahydrofuran or the like, at a temperature in the range of from about room temperature to the reflux temperature. The resulting compound of formula Ib can be recovered utilizing conventional methods, for example, crystallization, chromatography or the like.

This invention also relates to the pharmaceutically acceptable salts of the 3,4-dihydro-2H-1-benzopyran derivatives of formula I and their enantiomers, when $R^5$ is hydrogen. Said salts can be prepared by reacting an acid of formula I or an enantiomer thereof with a base having a non-toxic, pharmacologically and pharmaceutically acceptable cation. In general, any base which will form a salt with a carboxylic acid and whose pharmacological properties with not cause an adverse physiological effect when ingested by a warm-blood animal is considered as being within the scope of the invention. Suitable bases thus include, for example, alkali metal and alkaline earth metal hydroxides or carbonates, such as, sodium hydroxide, potassium hydroxide, calcium hydroxide, potassium carbonate and the like, ammonia, primary, secondary and tertiary amines, such as monoalkylamines, dialkylamines, trialkylamines, nitrogen containing heterocyclic amines, for example, piperidine, basic amino acids such as lysine, and the like. The pharmaceutically acceptable salts thus produced are the functional equivalent of the corresponding 3,4-dihydro-2H-1-benzopyranyloxy alkanoic acids of formula I and their enantiomers and one skilled in the art will appreciate that, to the extent that the salts of the invention are useful in therapy, the variety of salts encompassed by this invention are limited only by the criterion that the bases employed in forming the salts by both non-toxic and physiologically acceptable.

The useful antiallergic activity of the compounds of formula I and enantiomers thereof, including their pharmaceutically acceptable salts when $R^5$ is hydrogen, is demonstrated in vitro and in warm-blooded animals utilizing standard pharmacological procedures. Exemplary of such procedures are:

(a) Guinea Pig Ileum, In Vitro:

The guinea pig ileum biassay system has been described by Orange Austen, Adv. Immunol. 10: 105–144 (1969). A 1.5 cm segment is removed from animals weighing 300–400 g and suspended in an organ bath containing 10 ml of Tyrodes solution with $10^{-6}$M atropine sulfate and $10^{-6}$M pyrilamine maleate. The bath is maintained at 37° C. and aerated with a mixture of 95% oxygen and 5% carbon dioxide. The SRS-A utilized in this screen is obtained by challenging chopped lung fragments from actively sensitized guinea pigs with egg albumin, in vitro. A dose-response curve to SRS-A challenge is established for the ileum. The dose of SRS-A which given 50% of the maximal contraction (EC$_{50}$) is then used for subsequent challenge. The drug concentration which inhibits, by 50%, the SRS-A induced constriction of the guinea pig ileum is determined. In this bioassay system, the standard SRS-A antagonist, 7-[3-(4-acetyl-3-hydroxy-2-propylphenoxy)-2-hydroxypropyl]-4-oxo-8-propyl-4H-1-benzopyran-2-carboxylic acid, has an IC$_{50}$ of $3.5 \times 10^{-8}$M.

(b) Guinea Pig Bronchoconstriction, In Vivo (Aerosol):

Male guinea pigs (Hartley strain) weighing 300 to 500 g are anesthetized with urethane (2 g/kg) intraperitoneally and a polyetylene cannula is inserted into the jugular vein for drug administration. Tracheal pressure is recorded from a cannula inserted in the trachea and connected to a Statham pressure transducer. After surgical preparation of the animals, a period of time is allowed from pulmonary functions to stabilize. The test compound is administered according to the following protocol. Propanolol (0.1 mg/kg) is administered intravenously while the animals breathed spontaneously. Five minutes thereafter, the animals are exposed for a five minute period to a 1% (w/v) aerosol solution of test compound (adjusted to an alkaline pH where necessary for drug solubilization) or to distilled water of the appropriate pH (for control purposes). A Monaghan (Model 750) ultrasonic nebulizer is used to administer all test compounds by inhalation. The nebulizer ultrasonic frequency is adjusted to produce particles in the 1–8μ diameter range (average 3μ). Aqueous solutions are prepared freshly and introduced into the chamber of the nebulizeer. The output of the nebulizer is made available to the animal by directing a bias flow of aerosol through a Y tube connected to the tracheal cannula. At the end of the exposure period, the animals are paralyzed with succinylcholine (1.2 mg/kg, i.v.) and mechanically respirated (Harvard rodent respirator) at 40 breaths/minute and 2.5 cc tidal volume. Animals are then challenged with a maximum constrictory dose of leukotriene E$_4$ delivered intravenously 30 seconds after administration of the succinylcholine.

The change (cm H$_2$O) between pre and peak ventilatory pressure readings averaged for three control animals and five drug treated animals. The percent inhibition is calculated from the following formula:

$$\frac{\text{Control} - \text{Drug Treated}}{\text{control}} \times 100$$

When various drug concentrations are tested, the percent inhibition at each concentration is plotted as log concentration (abscissa) versus percent inhibition (ordinate) and the IC$_{50}$ is determined from linear regression analysis.

When compounds of formula I, as listed hereinafter in Tables I and II, were utilized in the test procedures described above, the result set out in Tables I and II were obtained:

TABLE I

SRS-A ANTAGONISM

| Test Compound | In vitro G.P. ileum IC$_{50}$ (M) |
|---|---|
| rac-[[2-[6-(4-acetyl-3-hydroxy-2-propylphenoxy)hexyl]-3,4-dihydro-2-methyl-4-oxo-8-propyl-2H—1-benzopyran-7-yl]oxy]acetic acid | $5 \times 10^{-7}$ |
| rac-[[2-[6-(4-acetyl-3-hydroxy-2-propylphenoxy)hexyl]-3,4-dihydro-4-oxo-8-propyl-2H—1-benzopyran-7-yl]oxy]-acetic acid | $3 \times 10^{-7}$ |
| rac-[[2-[4-(4-acetyl-3-hydroxy-2-propylphenoxy)butyl]-3,4-dihydro-4-oxo-8-propyl-2H—1-benzopyran-7-yl]oxy]-acetic acid | $5 \times 10^{-7}$ |
| rac-[[2-[4-(4-acetyl-3-hydroxy-2-propylphenoxy)butyl]-3,4-dihydro-2-methyl-4-oxo-2H—benzopyran-7-yl]oxy]-acetic acid | $5 \times 10^{-6}$ |
| rac-4-[[2-[4-(4-acetyl-3-hydroxy-2-propylphenoxy)butyl]-3,4-dihydro-2-methyl-4-oxo-2H—1-benzopyran-7-yl]oxy]-butanoic acid | $3 \times 10^{-6}$ |
| rac-[2-[4-(4-acetyl-3-hydroxy-2-propylphenoxy)butyl]-3,4-dihydro-2-methyl-4-oxo-8-propyl-2H—1-benzopyran-7-yl]oxy]acetic acid | $2 \times 10^{-6}$ |
| rac-4-[[2-[4-(4-acetyl-3-hydroxy-2-propylphenoxy)butyl]-3,4-dihydro-2-methyl-4-oxo-8-propyl-2H—1-benzopyran-7-yl]oxy]butanoic acid | $1 \times 10^{-6}$ |

TABLE II

SRS-A ANTAGONISM

| Test Compound | In vivo-aerosol IC$_{50}$ (%) or % inhib. at (% conc.) |
|---|---|
| rac-[[2-[6-(4-acetyl-3-hydroxy-2-propylphenoxy)hexyl]-3,4-dihydro-2-methyl-4-oxo-8-propyl-2H—1-benzopyran-7-yl]oxy]acetic acid | 0.26 |
| rac-[[2-[6-(4-acetyl-3-hydroxy-2- | 0.32 |

TABLE II-continued

SRS-A ANTAGONISM

| Test Compound | In vivo-aerosol IC$_{50}$ (%) or % inhib. at (% conc.) |
|---|---|
| propylphenoxy)hexyl]-3,4-dihydro-4-oxo-8-propyl-2H—1-benzopyran-7-yl]oxy]-acetic acid | |
| rac-[[2-[4-(4-acetyl-3-hydroxy-2-propylphenoxy)butyl]-3,4-dihydro-4-oxo-8-propyl-2H—1-benzopyran-7-yl]oxy]-acetic acid | 34.1 ± 8 (0.1) |

(c) Oral Testing of Leukotriene Antagonists

Male guinea pigs (Hartley strain, Charles River) weighing 400 to 600 g were anesthetized with urethane (2 g/kg) intraperitoneally and a polyethylene cannula was inserted into the jugular vein for intravenous drug administration. Tracheal pressure (cm water) was recorded from a Statham pressure transducer. After surgical preparation of the animals, a period of time was allowed for spontaneous breathing to stabilize. Since previous studies have demonstrated a potentiating effect of propanolol (0.1 mg/kg, i.v.) on bronchoconstriction induced with synthetic leukotriene, propanolol was administered five minutes prior to challenge with leukotriene. Two minutes later, spontaneous breathing was arrested with succinylcholine chloride (1.2 mg/kg, i.v.) and the animals ventilated with a Harvard (Model #680) small animal respirator set at 40 breaths per minute and 4.0 cc stroke volume. The animals were challenged with a maximum constrictory dose of either leukotriene C$_4$ or leukotriene D$_4$ or leukotriene E$_4$ (25 g/kg, i.v.) at 5 minutes. Control vehicle or test drug (adjusted to an alkaline pH where necessary for drug solubilization) was administered (10 mg/kg, p.o) two hours prior to challenge with leukotriene. In order to determine the ID$_{50}$ for a test drug, the dose is varied from 10 mg/kg, p.o. to 100, 50, 30, 20, 5, 3 and 1 mg/kg. p.o.

In order to determine oral duration of action, the time between exposure to test drug and challenge with leukotriene is varied.

In test procedure (c), the compounds listed in Table III were tested by this oral procedure, and the results obtained are also set out in Table III.

TABLE III

SRS-A ANTAGONISM

| Test Compound | % Inhib. of LTD$_4$ 10 mg/kg P.O. |
|---|---|
| rac-[[2-[4-(4-acetyl-3-hydroxy-2-propylphenoxy)butyl]-3,4-dihydro-2-methyl-4-oxo-2H—1-benzopyran-7-yl]oxy]acetic acid methyl ester | 47 ± 5 |
| rac-[[2-[4-(4-acetyl-3-hydroxy-2-propylphenoxy)butyl]-3,4-dihydro-2-methyl-4-oxo-8-propyl-2H—1-benzopyran-7-yl]oxy]acetic acid methyl ester | 25 ± 12 |
| rac-4-[[2-[4-(4-acetyl-3-hydroxy-2-propylphenoxy)butyl]-3,4-dihydro-2-methyl-4-oxo-8-propyl-2H—1-benzopyran-7-yl]oxy]butanoic acid ethyl ester | 38 ± 7 |

A compound of formula I, an enantiomer thereof or a salt thereof, when $R^5$ is hydrogen, or a composition containing a therapeutically effective amount of a compound of formula I, an enantiomer thereof or a salt thereof, when $R^5$ is hydrogen, can be administered by methods well known in the art. Thus, a compound of formula I, an enantiomer thereof or a salt thereof, when $R^5$ is hydrogen, can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example, in the form of an aerosol, micropulverized powder or nebulized solution. Presently, the most preferred route of administration for the compounds of formula I is by inhalation, for example, as an aerosol, and particularly for use as an antiasthmatic agent. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweentening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound formula I, an enantiomer thereof, or salt thereof, when $R^5$ is hydrogen, to be administered and the frequency of administration will be dependent on the potency and duration of activity of the particular compound of formula I, an enantiomer or salt thereof to be administered and on the route of administration, as well as the severity of the condition, age of the warm-blooded animal to be treated and the like. Doses of a compound of formula I, an enantiomer thereof or a salt thereof, when $R^5$ is hydrogen, contemplated for use in the practice of the invention are in the range of from about 25 to about 1000 mg per day, preferably about 25 to about 250 mg either as a single dose or in divided doses per day.

Since the compounds of formulas I of the invention possess an asymmetric carbon atom, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I, when $R^5$ is hydrogen, with an optically active resolving agent, for example, an optically active base, such as d-(+)-α-methylbenzylamine, which can be reacted with a carboxyl group. The formed diastereomers are separated by selective crystallization and converted to the corresponding optical isomer. Thus, the invention covers the racemates of the compounds of formula I, as well as their optically active isomers (enantiomers).

The examples which follow also further describe the invention. All temperatures given are in degree centigrade almost otherwise stated. All reactions were carried out under an inert atmosphere.

EXAMPLE 1

Preparation of rac.-2,3-dihydro-2-[6-[(tetrahydro-2H-pyran-2-yl)oxy]-hexyl]-7-hydroxy-2-methyl-8-propyl-4H-1-benzopyran-4-one A mixture of 2.9 g of 8-hydroxy-2-octanone tetrahydropyranyl ether (C. Bernasconi et al., Bull. Soc. Chim. Fr., 107 (1977)), 2.46 g of 2,4-dihydroxy-3-n-propylacetophenone, 25 ml of toluene, and 1.05 ml of pyrrolidine was stirred at room temperature for 20 hours then refluxed for 3.5 hours using a Dean-Stark trap for water removal. The mixture was cooled, treated with 20 ml of 3N hydrochloric acid and stirred for 20 minutes. The mixture was diluted with water and extracted with ether. The combined ether extracts were washed with 3N hydrochloric acid, water, saturated sodium bicarbonate, brine and then dried (magnesium sulfate) filtered and concentrated in vacuo. The residual red oil was purified by high performance liquid chromatography (HPLC) (silica gel; 2:1 hexane-ethyl acetate) giving 3.0 g (58.5%) of rac-2,3-dihydro-2-[6-[(tetrahydro-2H-pyran-2-yl)oxy]hexyl]-7-hydroxy-2-methyl-8-propyl-4H-1-benzopyran-4-one as a reddish oil.

EXAMPLE 2

Preparation of rac.-[[3,4-dihydro-2-[6-[(tetrahydro-2H-pyran-2-yl)oxy]hexyl]-2-methyl-4-oxo-8-propyl-2H-1-benzopyran-7-yl]oxy]acetic acid methyl ester A mixture of 0.706 g of rac.-2,3-dihydro-2-[6-[(tetrahydro-2H-pyran-2-yl)oxy]hexyl]-7-hydroxy-2-methyl-8-propyl-4H-1-benzopyran-4-one, 16 ml of N,N-dimethylformamide, and 0.477 g of anhydrous potassium carbonate was stirred at room temperature for 2 hours. A 0.33 ml (0.53 g) portion of methyl bromoacetate was added and stirring was continued for 17.5 hours at room temperature. The mixture was poured into water and the pH was adjusted to 7 with 0.5N hydrochloric acid. The organic product was isolated by extraction with 3 portions of ether. The ether extracts were combined, washed with water and brine, dried over anhydrous magnesium sulfate filtered and concentrated in vacuo to give a yellow oil. This material was purified by high pressure liquid chromatography (HPLC) (silica gel, 2:1 hexane-ethyl acetate) yielding 0.589 g (70.8%) of rac.-[[3,4-dihydro-2-[6-[(tetrahydro-2H-pyran-2-yl)oxy]hexyl]-2-methyl-4-oxo-8-propyl-2H-1-benzopyran-7-yl]oxy]acetic acid methyl ester as a pale-yellow oil.

Analysis Calculated for $C_{27}H_{40}O_7$: C, 68.04; H, 8.46. Found: C, 67.87; H, 8.20.

EXAMPLE 3

Preparation of rac.-[[3,4-dihydro-2-(6-hydroxyhexyl)-2-methyl-4-oxo-8-propyl-2H-1-benzopyran-7-yl]oxy]acetic acid methyl ester A solution of 2.3 g of the chromanone product from Example 2 in 25 ml of methanol and 5 ml of 2N hydrochloric acid was stirred for 1.75 hours at room temperature then concentrated in vacuo to remove most of the methanol. The residue was diluted with water, neutralized with sodium bicarbonate, and extracted 4 times with ether. The combined ether extracts were washed with water and brine, dried (magnesium sulfate), filtered, and concentrated in vacuo in yield 1.85 g of an oil. This material was purified by HPLC (silica gel, 1.5:1 ethyl acetate-hexane) giving 1.65 g (87.1%) of rac.-[[3,4-dihydro-2-(6-hydroxyhexyl)-2-methyl-4-oxo-8-propyl-2H-1-benzopyran-7-yl]oxy]acetic acid methyl ester as a yellow oil.

Analysis Calculated for $C_{22}H_{32}O_6$: C, 67.32; H, 8.22, Found: C, 67.07; H, 8.43.

EXAMPLE 4

Preparation of rac.-[[3,4-dihydro-2-(6-iodohexyl)-2-methyl-4-oxo-8-propyl-2H-1-benzopyran-7-yl]oxy]acetic acid methyl ester A solution of 1.14 g of the hydroxyhexyl chromanone product from Example 3 in 28 ml of dichloromethane and 1.03 ml (0.75 g), of triethylamine was treated with 0.54 ml (0.804 g) of methanesulfonyl chloride. The mixture was stirred at room temperature for 2 hours then poured into water and extracted with 3 portions of dichloromethane. The organic extracts were combined, washed with brine, dried (magnesium sulfate), filtered and concentrated in vacuo giving 1.5 g of the methanesulfonate derivative as a yellow oil. This material was dissolved in 40 ml of acetone and 1.91 g of sodium iodide was added. The mixture was stirred at room temperature for 67 hours then poured into water and extracted 4 times with ether. The combined ether extracts were washed with aqueous sodium bicarbonate, water, and brine, then dried (magnesium sulfate), filtered and concentrated in vacuo giving 1.32 g (90.4%) of rac.-[[3,4-dihydro-2-(6-iodohexyl)-2-methyl-4-oxo-8-proppyl-2H-1-benzopyran-7-yl]oxy]acetic acid methyl ester as a yellow oil which crystallized on standing, m.p. 53°–60° C.

EXAMPLE 5

Preparation of rac.-[[2-[6-(4-acetyl-3-hydroxy-2-propylphenoxy)hexyl]-3,4-hydroxy-2-methyl-4-oxo-8-propyl-2H-1-benzopyran-7-yl]oxy]acetic acid methyl ester A mixture of 1.25 g of the iodohexyl chromanone product from Example 4, 0.49 g of 2,4-dihydroxy-3-propylacetophenone, 0.841 g of anhydrous potassium bicarbonate, 25 ml of acetone, and 12 ml of N,N-dimethylformamide was refluxed and stirred for 6 hours. The resulting mixtures was cooled, poured into cold 1N hydrochloric acid, and extracted 3 times with ether. The combined ether extracts were washed with saturated aqueous sodium bicarbonate, water, and brine, then dried (magnesium sulfate), filtered and concentrated in vacuo giving 1.5 g of an oil. This material was chromatographed on 45 g of silica gel. Elution with 2:1 hexane-ethyl acetate afforded 1.18 g (83.4%) of rac-[[2-[6-(4-acetyl-3-hydroxy-2-propylphenoxy)-hexyl]-3,4-dihydro-2-methyl-4-oxo-8-propyl-2H-1-benzopyran-7-yl]oxy]acetic acid methyl ester as a colorless oil.

Analysis Calculated for $C_{33}H_{44}O_8$: C, 69.70; H, 7.80. Found: C, 69.68; H, 8.00.

EXAMPLE 6

Preparation of rac.-[[2-[6-(4-acetyl-3-hydroxy-2-propylphenoxy)hexyl]-3,4-dihydro-2-methyl-4-oxo-8-propyl-2H-1-benzopyran-7-yl]oxy]acetic acid A solution of 1.1 g of the ester product from Example 5 and 0.966 g of sodium hydroxide, in 36 ml of methanol and 9 ml of water was stirred at room temperature for 5.5 hours then poured into 60 ml of cold 1N hydrochloric acid and 150 ml of water. The mixture was extracted 3 times with ether. The combined ether extracts were washed with 3 portions of saturated aqueous sodium bicarbonate. Each bicarbonate wash was back-extracted with ether. The bicarbonate washes were combined and acidified to pH 1 with 3N hydrochloric acid. The acidic mixture was extracted 3 times with ethyl acetate. The ethyl acetate extracts were combined, washed with water and brine, dried (magnesium sulfate), filtered and concentrated in vacuo to yield 1.04 g of a yellow solid. This material was recrystallized from acetonitrile giving 0.82 g (76.6%) of rac.-[[2-[6-(4-acetyl-3-hydroxy-2-propylphenoxy)hexyl]-3,4-dihydro-2-methyl-4-oxo-8-propyl-2H-1-benzopyran-7-yl]oxy]acetic acid as a colorless solid, m.p. 120.5°–125.0° C.

Analysis Calculated for $C_{32}H_{42}O_8$: C, 69.29; H, 7.53. Found: C, 69.46; H, 7.64.

EXAMPLE 7

Preparation of rac.-2,3-dihydro-2-[6-[(tetrahydro-2H-pyran-2-yl)oxy]-hexyl]-7-hydroxy-8-propyl-4H-1-benzopyran-4-one A mixture of 4.8 g of 7-hydroxyheptanal tetrahydropyranyl ether (Schwartz et al., J. Org. Chem. 40, 2410 (1975), 4.34 g of 2,4-dihydroxy-3-propylacetophenone 360 ml of benzene, and 4.77 ml (3.93 g) of pyrrolidine was stirred at room temperature for 21 hours, the refluxed for 7 hours with water removal by means of a Dean-Stark trap. The mixture was cooled and poured into 270 ml of water containing 55 ml of 1N hydrochloric acid. The two-phase mixture was stirred at room temperature for 25 minutes then extracted 4 times with ether. The ether extracts were combined, washed with water and brine, dried (magnesium sulfate), filtered and concentrated in vacuo giving 12 g of a red oil. This material was dissolved in 2:1 hexane-ethyl acetate and the solution was filtered through a pad of silica gel. The silica gel was washed with 2.51 of 2:1 hexane-ethyl acetate. The combined filtrate and washes were concentrated in vacuo giving a red oily residue which was further purified by HPLC (silica gel, 2:1 hexane-ethyl acetate). There was obtained 2.05 g (23.5%) of rac.-2,3-dihydro-2-[6-[(tetrahydro-2H-pyran-2-yl)oxy]-hexyl]-7-hydroxy-8-propyl-4H-1-benzopyran-4-one as a yellow oil.

EXAMPLE 8

Preparation of rac.-[[3,4-dihydro-2-[6-[(tetrahydro-2H-pyran-2-yl)oxy]hexyl]-4-oxo-8-propyl-2H-1-benzopyran-7-yl]oxy]acetic acid methyl ester Using the procedure of Example 2, the chromanone product from Example 7 was converted into rac.-[[3,4-dihydro-2-[6-[(tetrahydro-2H-pyran-2-yl)oxy]hexyl]-4-oxo-8-propyl-2H-1-benzopyran-7-yl]oxy]acetic acid methyl ester, a yellow oil, in 84.9% yield.

Analysis Calculated for $C_{26}H_{38}O_7$: C, 67.51; H, 8.28. Found: C, 66.82; H, 8.44.

EXAMPLE 9

Preparation of rac.-[[3,4-dihydro-2-(6-hydroxyhexyl)-4-oxo-8-propyl-2H-1-benzopyran-7-yl]oxy]acetic acid methyl ester Using the procedure of Example 3, the chromanone ester product from Example 8 was converted into rac.-[[3,4-dihydro-2-(6-hydroxyhexyl)-4-oxo-8-propyl-2H-1-benzopyran-7-yl]oxy]acetic acid methyl ester, a colorless solid, m.p. 93°–94.5° C. (from ethyl acetate-hexane), in 90% yield.

Analysis Calculated for $C_{21}H_{30}O_6$: C, 66.65; H, 7.99. Found: C, 66.89; H, 8.08.

EXAMPLE 10

Preparation of rac.-[[3,4-dihydro-2-(6-iodohexyl)-4-oxo-8-propyl-2H-1-benzopyran-7-yl]oxy]acetic acid methyl ester Using the procedure of Example 4, the hydroxyhexyl chromanone product from Example 9 was converted into rac.[[3,4-dihydro-2-(6-iodohexyl)-4-oxo-8-propyl-2H-1-benzopyran-7-yl]oxy]acetic acid methyl ester, a yellow oil.

EXAMPLE 11

Preparation of rac.-[[2-[6-(4-acetyl-3-hydroxy-2-propylphenoxy)hexyl]-3,4-dihydro-4-oxo-8-propyl-2H-1-benzopyran-7-yl]oxy]acetic acid methyl ester Using the procedure of Example 5, the iodohexyl chromanone product from Example 10 was converted into rac.-[[2-[6-(4-acetyl-3-hydroxy-2-propylphenoxy)hexyl]-3,4-dihydro-4-oxo-8-propyl-2H-1-benzopyran-7-yl]oxy]acetic acid methyl ester, a colorless solid, m.p. 121°–123.5° C. (from acetonitrile), in 69.5% yield.

Analysis Calculated for $C_{32}H_{42}O_8$: C, 69.29; H, 7.63. Found: C, 69.00; H, 7.89.

EXAMPLE 12

Preparation of rac.-[[2-[6-(4-acetyl-3-hydroxy-2-propylphenoxy)hexyl]-3,4-dihydro-4-oxo-8-propyl-2H-1-benzopyran-7-yl]oxy]acetic acid Using the procedure of Example 6, the ester product from Example 11 was saponified giving rac.-[[2-[6-(4-acetyl-3-hydroxy-2-propylphenoxy)hexyl]-3,4-dihydro-4-oxo-8-propyl-2H-1-benzopyran-7-yl]oxy]acetic acid, a colorless solid m.p. 168°–173° C. (from ethyl acetate), in 84% yield.

Analysis Calculated for $C_{31}H_{40}O_8$: C, 68.86; H, 7.45. Found: C, 68.75; H, 7.60.

EXAMPLE 13

Preparation of rac.-7-hydroxy-2,3-dihydro-2-[4-[(tetrahydro-2H-pyran-2-yl)oxy]butyl]-8-propyl-4H-1-benzopyran-4-one Using the procedure of Example 7, 5-hydroxypentanal tetrahydropyranyl ether (Hurd and Richardson, J. Org. Chem. 32, 3516 (1967)) was condensed with 2,4-dihydroxy-3-propylacetophenone giving rac.-7-hydroxy-2,3-dihydro-2-[4-[(tetrahydro-2H-pyran-2-yl)oxy]butyl]-8-propyl-4H-1-benzopyran-4-one, a yellow oil, in 24% yield.

EXAMPLE 14

Preparation of
rac.-[[3,4-dihydro-2-[4-tetrahydro-2H-pyran-2-yl]oxy]-
butyl]-4-oxo-8-propyl-2H-1-benzopyran-7-yl]oxy]-
acetic acid methyl ester Using the procedure of Example 2, the hydroxy chromanone product from Example 13 was converted into rac.-[[3,4-dihydro-2-[(4-tetrahydro-2H-pyran-2-yl)oxy]butyl]-4-oxo-8-propyl-2H-1-benzopyran-7-yl]oxy]acetic acid methyl ester, a yellow oil, in 87.4% yield.

EXAMPLE 15

Preparation of
rac.-[[3,4-dihydro-2-(4-hydroxybutyl)-4-oxo-8-propyl-
2H-1-benzopyran-7-yl]oxy]acetic acid methyl ester Using the procedure of Example 3, the chromanone ester product from Example 14 was converted into rac.-[[3,4-dihydro-2-(4-hydroxybutyl)-4-oxo-8-propyl-2H-1-benzopyran-7-yl]oxy]acetic acid methyl ester, a yellow oil, in 68% yield.

EXAMPLE 16

Preparation of
rac.-[[3,4-dihydro-2-(4-iodobutyl)-4-oxo-8-propyl-2H-1-
benzopyran-7-yl]oxy]acetic acid methyl ester Using the procedure of Example 4, the hydroxybutyl chromanone product from Example 15 was converted into rac.-[[3,4-dihydro-2-(4-iodobutyl)-4-oxo-8-propyl-2H-1-benzopyran-7-yl]oxy]acetic acid methyl ester, a yellow oil.

EXAMPLE 17

Preparation of
rac.-[[2-[4-(4-acetyl-3-hydroxy-2-propylphenoxy)-
butyl]-3,4-dihydro-4-oxo-8-propyl-2H-1-benzopyran-7-
yl]oxy]acetic acid methyl ester Using the procedure of Example 5, the iodobutyl chromanone product from Example 16 was converted into rac.-[[2-[4-(4-acetyl-3-hydroxy-2-propylphenoxy)-butyl]-3,4-dihydro-4-oxo-8-propyl-2H-1-benzopyran-7-yl]oxy]acetic acid methyl ester, a colorless solid, in 70% yield.

EXAMPLE 18

Preparation of
rac.-[[2-[4-(4-acetyl-3-hydroxy-2-propylphenoxy)-
butyl]-3,4-dihydro-4-oxo-8-propyl-2H-1-benzopyran-7-
yl]oxy]acetic acid A solution of 0.3 g of the ester product from Example 17 and 0.48 g of lithium hydroxide monohydrate in 10 ml of 1:1 water-tetrahydrofuran was stirred at room temperature for 24 hours then diluted with water and extracted with ether (the ether extract was discarded). The aqueous solution was acidified with 1N hydrochloric acid and extracted 3 times with ether. The ether extracts were combined, dried (magnesium sulfate), filtered and concentrated in vacuo giving a solid residue which was chromatographed on 12 g of silica gel. Elution with tetrahydrofuran gave the acid which was recrystallized from methanol yielding rac.-[[2-[4-(4-acetyl-3-hydroxy-2-propylphenoxy)butyl]-3,4-dihydro-4-oxo-8-propyl-2H-1-benzopyran-7-yl]oxy]acetic acid as an off-white solid, m.p. 163.5°–167.0° C.

Analysis calculated for $C_{29}H_{36}O_8$: C, 67.95; H, 7.08. Found: C, 67.73; H, 7.14.

EXAMPLE 19

Preparation of
rac.-2,3-dihydro-2-[4-[(tetrahydro-2H-pyran-2-yl)oxy]-
butyl]-2-methyl-7-hydroxy-8-propyl-4H-1-benzopyran-
4-one A mixture of 2.54 g of 6-hydroxy-2-hexanone tetrahydropyranyl ether, 2.46 g of 2,4-dihydroxy-3-propylacetophenone, 1.05 g of pyrrolidine, and 35 ml of toluene was stirred at room temperature for four days. The dark brown solution was then refluxed for 24 hours, with water removal using a Dean-Stark trap. A mixture of 1:1 ethylacetate-toluene (400 ml) and 50 g of silica were added to the reaction mixture and the slurry was stirred for 1 hour at room temperature. The silica gel was filtered with suction and washed with 1:1 ethyl acetate-toluene. The filtrate and washes were combined and concentrated in vacuo. The residual oil was purified by column chromatography on silica gel. Hexane-ethyl acetate (2:1) eluted 3.3 g (69.1%) of rac.-2,3-dihydro-2-[4-[(tetrahydro-2H-pyran-2-yl)oxy]butyl]-2-methyl-7-hydroxy-8-propyl-4H-1-benzopyran-4-one, as a dark brown oil.

EXAMPLE 20

Preparation of
rac.-[[3,4-dihydro-2-[4-(tetrahydro-2H-pyran-2-yl)oxy]-
butyl]-2-methyl-4-oxo-8-propyl-2H-1-benzopyran-7-
yl]oxy]acetic acid methyl ester A mixture of 3.3 g of the hydroxy chromanone product from Example 19, 1.45 g of methyl bromoacetate, 2.41 g of anhydrous potassium carbonate and 60 ml of acetone was stirred and refluxed for 17 hours. After being cooled, the reaction mixture was poured into 200 ml of water. The organic product was isolated by extraction with ethyl acetate. The extracts were combined, washed with water, and brine, dried over anhydrous magnesium sulfate filtered and the solvent evaporated in vacuo to give 3.5 g of a red oil. Purification of this material by chromatography on a silica gel column (eluting system 4:1 hexane-ethyl acetate) yielding 2.52 g (64.1%) of rac.-[[3,4-dihydro-2-[4-(tetrahydro-2H-pyran-2-yl)oxy]butyl]-2-methyl-4-oxo-8-propyl-2H-1-benzopyran-7yl]-oxy]acetic acid methyl ester, as a yellow oil.

EXAMPLE 21

Preparation of
rac.-[[3,4-dihydro-2-(4-hydroxybutyl)-2-methyl-4-oxo-
8-propyl-2H-1-benzopyran-7-yl]oxy]acetic acid methyl
ester Using the procedure of Example 3, the chromanone ester product from Example 20 was converted into rac.-[[3,4-dihydro-2-(4-hydroxybutyl)-2-methyl-4-oxo-8-propyl-2H-1-benzopyran-7-yl]oxy]acetic acid methyl ester, an amber oil, in 99% yield.

EXAMPLE 22

Preparation of
rac.-[[3,4-dihydro-2-(4-iodobutyl)-4-oxo-2-methyl-8-
propyl-2H-1-benzopyran-7-yl]oxy]acetic acid methyl
ester Using the procedure described in Example 4, the hydroxy chromanone product from Example 21 was converted into rac.-[[3,4-dihydro-2-(4-iodobutyl)-4- oxo-2-methyl-8-propyl-2H-1-benzopyran-7-yl]oxy]acetic acid methyl ester, a yellow oil, in 53% yield.

Analysis Calculated for $C_{20}H_{27}IO_3$: C, 50.64; H, 5.76 I, 26.75. Found: C, 50.42; H, 5.61; I, 26.68.

EXAMPLE 23

Preparation of rac.-[[2-[4-(4-acetyl-3-hydroxy-2-propylphenoxy)-butyl]-3,4-dihydro-2-methyl-4-oxo-8-propyl-2H-1-benzopyran-7-yl]oxy]acetic acid methyl ester Using the procedure of Example 5, the iodobutyl chromanone product from Example 22 was converted into rac.-[[2-[4-(4-acetyl-3-hydroxy-2-propylphenoxy)-butyl]-3,4-dihydro-2-methyl-4-oxo-8-propyl-2H-1-benzopyran-7-yl]oxy]acetic acid methyl ester, a yellow oil, in 84% yield.

Analysis Calculated for $C_{31}H_{40}O_8$: C, 68.87; H, 7.46. Found: C, 68.39; H, 7.56.

EXAMPLE 24

Preparation of rac.-[2-[4-(4-acetyl-3-hydroxy-2-propylphenoxy)butyl]-3,4-dihydro-2-methyl-4-oxo-8-propyl-2H-1-benzopyran-7-yl]oxy]acetic acid A solution of 1.05 g of the chromanone ester from Example 23 and 0.93 g of lithium hydroxide mnonhydrate in 20 ml of 1:1 tetrahydrofuran-water was stirred at room temperature for 5 hours. The reaction mixture was poured into 25 ml of 1N hydrochloric acid and extracted with ethyl acetate. The organic extract was washed with saturated brine, dried (magnesium sulfate), filtered, and the solvent evaporated in vacuo to give 935 mg of a pink solid. Crystallization from ethyl/acetate-hexane yielded 654 mg (64%) of rac.-[2-[4-(4-acetyl-3-hydroxy-2-propylphenoxy)butyl]-3,4-dihydro-2-methyl-4-oxo-8-propyl-2H-1-benzopyran-7-yl]oxy]acetic acid as a pink solid, m.p. 118°–126° C.

Analysis Calculated for $C_{30}H_{38}O_8$: C, 68.42; H, 7.27. Found: C, 68.38; H, 7.25.

EXAMPLE 25

Preparation of rac.-[[3,4-dihydro-2-[4-(tetrahydro-2H-pyran-2-yl)oxy]-butyl]-2-methyl-4-oxo-8-propyl-2H-1-benzopyran-7-yl]oxy]butanoic acid ethyl ester Using the procedure described in Example 20, 3.47 g of the hydroxy chromanone product from Example 19 was alkylated with 1.97 g of ethyl 4-bromobutyrate to yield 1.69 g (37.3%) of rac.-[[3,4-dihydro-2-[4-(tetrahydro-2H-pyran-2-yl)oxy]butyl]-2-methyl-4-oxo-8-propyl-2H-1-benzopyran-7-yl]oxy]butanoic acid ethyl ester as a yellow oil after purification of the crude product by column chromatography on silica gel.

EXAMPLE 26

Preparation of rac-[(3,4-dihydro-2-(4-hydroxybutyl)-2-methyl-4-oxo-8-propyl-2H-1-benzopyran-7-yl]oxy]butanoic acid ethyl ester Using the procedure of Example 3, the chromanone ester product from Example 25 was hydrolyzed to rac.-[(3,4-dihydro-2-(4-hydroxybutyl)-2-methyl-4-oxo-8-propyl-2H-1-benzopyran-7-yl]oxy]butanoic acid ethyl ester as a yellow oil, in 99% yield.

EXAMPLE 27

Preparation of rac.-[[3,4-dihydro-2-(4-iodobutyl)-4-oxo-2-methyl-8-propyl-2H-1-benzopyran-7-yl]oxy]butanoic acid ethyl ester Using the procedure of Example 4, the hydroxy chromanone product from Example 26 was converted into rac.-[[3,4-dihydro-2-(4-iodobutyl)-4-oxo-2-methyl-8-propyl-2H-1-benzopyran-7-yl]oxy]butanoic acid ethyl ester, a yellow oil, in 73.3% yield.

Analysis Calculated for $C_{23}H_{33}IO_5$; C, 53.49; H, 6.44; I, 24.57. Found: C, 53.75; H, 6.52; I, 24.38.

EXAMPLE 28

Preparation of rac.-4-[2-[4-(4-acetyl-3-hydroxy-2-propylphenoxy)-butyl]-3,4-dihydro-2-methyl-4-oxo-8-propyl-2H-1-benzopyran-7-yl]oxy]butanoic acid ethyl ester A mixture of 1.39 g of the iodobutyl chromanone product from Example 27, 0.876 g of anhydrous potassium carbonate, 0.522 g of 2,4-dihydroxy-3-propylacetophenone, 25 ml of acetone, and 25 ml of N,N-dimethylformamide was refluxed and stirred for 20 hours. The reaction mixture was cooled, poured into cold 1N hydrochloric acid and extracted with ethyl acetate. The organic extract was washed with water and saturated brine, then dried (magnesium sulfate), filtered, and concentrated in vacuo giving 1.99 g of an oil. Purification of this material by column chromatography on silica gel (elution system 2:1 hexane-ethyl acetate) yielded 1.38 g (87.3%) of rac.-4-[2-[4-(4-acetyl-3-hydroxy-2-propylphenoxy)butyl]-3,4-dihydro-2-methyl-4-oxo-8-propyl-2H-1-benzopyran-7-yl]oxy]-butanoic acid ethyl ester as a yellow oil.

Analysis Calculated for $C_{34}H_{46}O_8$: C, 70.08; H, 7.96. Found: C, 69.94; H, 7.84.

EXAMPLE 29

Preparation of rac.-4-[[2-[4-(4-acetyl-3-hydroxy-2-propylphenoxy)-butyl]-3,4-dihydro-2-methyl-4-oxo-8-propyl-2H-1-benzopyran-7-yl]oxy]butanoic acid Using the procedure of Example 24, the chromanone ester from Example 28 was converted by saponification into rac.-4-[[2-[4-(4-acetyl-3-hydroxy-2-propylphenoxy)butyl]-3,4-dihydro-2-methyl-4-oxo-8-propyl-2H-1-benzopyran-7-yl]oxy]butanoic acid, a yellow solid, in 94.5% yield.

Analysis Calculated for $C_{32}H_{42}O_8$: C, 69.29; H, 7.63. Found: C, 68.94; H, 7.65.

EXAMPLE 30

Preparation of rac.-2,3-dihydro-2-[4-[(tetrahydro-2H-1-pyran-2-yl)oxy]butyl]-2-methyl-7-hydroxy-4H-1-benzopyran-4-one A mixture of 8.7 g of 6-hydroxyhexanone tetrahydropyranyl ether, 6.61 g of 2,4-dihydroxyacetophenone, 5.43 g of pyrrolidine and 43 ml of toluene was stirred at room temperature for 18 hours then refluxed for 3 hours using a Dean-Stark trap for water removal. The mixture was cooled, diluted with 200 ml of ethyl acetate and 170 ml of toluene and treated with 100 g of silica gel. After being stirred for 19 hours, the slurry was suction filtered and the solids washed with 1:1 ethyl acetate-toluene. The filtrate and washes were combined and concentrated in vacuo to give 13.3 g of a red oil. Purification of this crude material by column chromatography on silica gel (eluting system 9:1 toluene-ethyl acetate) yielded 7.4 g (49.4%) of rac.-2,3-dihydro-2-[4-[(tetrahydro-2H-1-pyran-2-yl)oxy]butyl]-2-methyl-7-hydroxy-4H-1-benzopyran-4-one as a reddish oil.

EXAMPLE 31

Preparation of rac.-[[3,4-dihydro-2-[4-[tetrahydro-2H-pyran-2-yl)oxy]-butyl]-4-oxo-2H-1-benzopyran-7-yl]oxy]-butanoic acid ethyl ester Using the procedure of Example 2, the 7-hydroxy chromanone from Example 30 was converted into rac.-[[3,4-dihydro-2-[4-[tetrahydro-2H-pyran-2-yl)oxy]-butyl]-4-oxo-2H-1-benzopyran-7-yl]oxy]butanoic acid ethyl ester, a yellow oil, in 86.0% yield, by alkylation with ethyl 4-bromobutanoate.

EXAMPLE 32

Preparation of rac.-[3,4-dihydro-2-(4-hydroxybutyl)-2-methyl-4-oxo-2H-1-benzopyran-7-yl]oxy]butanoic acid ethyl ester Using the procedure of Example 3, the chromanone ester from Example 31 was hydrolyzed to yield rac.-[3,4-dihydro-2-(4-hydroxybutyl)-2-methyl-4-oxo-2H-1-benzopyran-7-yl]oxy]-butanoic acid ethyl ester a yellow oil, in 95% yield.

EXAMPLE 33

Preparation of rac.-[[3,4-dihydro-2-(4-iodobutyl)-4-oxo-2-methyl-2H-1-benzopyran-7-yl]oxy]butanoic acid ethyl ester Using the procedure described in Example 4, the hydroxy chromanone product from Example 32 was converted into rac.-[[3,4-dihydro-2-(4-iodobutyl)-4-oxo-2-methyl-2H-1-benzopyran-7-yl]oxy]butanoic acid ethyl ester, a viscous oil, in 65.7% yield.

Analysis Calculated for $C_{20}H_{27}IO_5$: C, 50.64; H, 5.74; I, 26.75. Found: C, 50.52; H; 5.69; I, 26.90.

EXAMPLE 34

Preparation of rac.-[[2-[4-(4-acetyl-3-hydroxy-2-propylphenoxy)-butyl]-3,4-dihydro-4-oxo-2H-1-benzopyran-7-yl]oxy]-butanoic acid ethyl ester Using the procedure of Example 5, the iodobutyl chromanone product from Example 33 was converted into rac.-[[2-[4-(4-acetyl-3-hydroxy-2-propylphenoxy)-butyl]-3,4-dihydro-4-oxo-2H-1-benzopyran-7-yl]oxy]-butanoic acid ethyl ester, a yellow oil in 96.5% yield.

Analysis Calculated for $C_{31}H_{40}O_8$: C, 68.87; H, 7.46. Found: C, 68.67; H, 7.43.

EXAMPLE 35

Preparation of rac.-4-[[2-[4-(4-acetyl-3-hydroxy-2-propylphenoxy)-butyl]-3,4-dihydro-2-methyl-4-oxo-2H-1-benzopyran-7-yl]oxy]butanoic acid Using the procedure of Example 24, the chromanone ester from Example 34 was saponified giving rac.-4-[[2-[4-(4-acetyl-3-hydroxy-2-propylphenoxy)-butyl]-3,4-dihydro-2-methyl-4-oxo-2H-1-benzopyran-7-yl]oxy]butanoic acid in 92.9% yield, as an amber oil.

Analysis Calculated for $C_{29}H_{36}O_8$: C, 67.95; H, 7.08. Found: C, 67.84; H, 7.28.

EXAMPLE 36

Preparation of rac.-[[3,4-dihydro-2-[4-(4-(tetrahydro-2H-pyran-2-yl)oxy]butyl]-2-methyl-4-oxo-2H-1-benzopyran-yl]-oxy]acetic acid methyl ester A mixture of 6 g of the hydroxy chromanone product from Example 30, 1.9 ml (3.07 g) of methyl bromoacetate, 5.1 g of anhydrous potassium carbonate, 15 ml of N,N-dimethylformamide, and 5 ml of acetone was stirred at room temperature for 1 hour then at 80° C. for 24 hours. After being cooled, the resulting slurry was diluted with ether and cautiously treated with 37 ml of 1N hydrochloric acid. The mixture was diluted with water and extracted with ether. The ether extracts were combined, washed with water and saturated brine, dried (magnesium sulfate), filtered and concentrated under reduced pressure. After drying the residue under high vacuum, there was obtained 5.5 g (75.2%) of rac.-[[3,4-dihydro-2-[4-(tetrahydro-2H-pyran-2-yl)oxy]-butyl]-2-methyl-4-oxo-2H-1-benzopyran-7-yl]oxy]a-cetic acid methyl ester as a viscous, orange oil.

EXAMPLE 37

Preparation of rac.-[[3,4-dihydro-2-(4-hydroxybutyl)-2-methyl-4-oxo-2H-1-benzopyran-7-yl]acetic acid methyl ester A solution of the chromanone ester from Example 36 (5.5 g) and 14 ml of 2N hydrochloric acid in 70 ml of methanol was stirred at room temperature for 4.5 hours. Most of the methanol was then removed under water aspirator pressure, at 40° C. The residue was diluted with water and extracted with ether. The ether extracts were combined, washed with water and brine, dried (magnesium sulfate) filtered, and concentrated under reduced pressure. The oily residue was dissolved in ether-ethyl acetate and the solution was washed twice with saturated sodium bicarbonate solution and saturated brine then dried (magnesium sulfate), filtered, and concentrated under reduced pressure. After being dried under high vacuum, the residue of rac.-[[3,4-dihydro-2-(4-hydroxybutyl)-2-methyl-4-oxo-2H-1-benzopyran-7-yl]oxy]acetic acid methyl ester (3.75 g; 86.2%) was obtained as a viscous, amber oil.

EXAMPLE 38

Preparation of rac.-[[3,4-dihydro-2-(4-iodobutyl)-4-oxo-2-methyl-2H-1-benzopyran-7-yl]oxy]acetic acid methyl ester Using the procedure described in Example 4, the hydroxy chromanone ester product from Example 37 was converted into rac.-[[3,4-dihydro-2-(4-iodobutyl)-4-oxo-2-methyl-2H-1-benzopyran-7-yl]oxy]acetic acid methyl ester as a yellow oil, in 86.3% yield.

EXAMPLE 39

Preparation of rac.-[[2-[4-(4-acetyl-3-hydroxy-2-propylphenoxy)-butyl]-3,4-dihydro-2-methyl-4-oxo-2H-1-benzopyran-7-yl]oxy]acetic acid methyl ester Using the procedure of Example 5, the iodobutyl chromanone product from Example 38 was converted into rac.-[[2-[4-(4-acetyl-3-hydroxy-2-propylphenoxy)-butyl]-3,4-dihydro-2-methyl-4-oxo-2H-1-benzopyran-7-yl]oxy]acetic acid methyl ester, a yellow oil, in 78.8% yield.

EXAMPLE 40

Preparation of rac.-[[2-[4-(4-acetyl-3-hydroxy-2-propylphenoxy)-butyl]-3,4-dihydro-2-methyl-4-oxo-2H-1-benzopyran-7-yl]oxy]acetic acid Using the procedure of Example 24, the chromanone ester from Example 39 was saponified with lithium hydroxide in tetrahydrofuran-water giving rac.-[[2-[4-(4-acetyl-3-hydroxy-2-propylphenoxy)-butyl]-3,4-dihydro-2-methyl-4-oxo-2H-1-benzopyran-7-yl]oxy]acetic acid in 97.9% yield, as a viscous, amber oil.

Analysis Calculated for $C_{27}H_{32}O_8$; C, 66.93; H, 6.66. Found: C, 66.46; H, 6.80.

EXAMPLE 41

Aerosol Formulation (Freon Suspension Aerosol)

| Ingredients | mg/100 μl | | |
|---|---|---|---|
| | 1 mg | 10 mg | 25 mg |
| rac-[[2-[6-(4-Acetyl-3-hydroxy-2-propylphenoxy)-hexyl]-3,4-dihydro-2-methyl-4-oxo-8-propyl-2H—1-benzopyran-7-yl]oxy]acetic acid (micronized) | 1 mg | 10 mg | 25 mg |
| Glyceryl Trioleate | 0.03 mg | 3.0 mg | 7.5 mg |
| Freon 114* 30 Parts ⎫ To<br>Freon 12 70 Parts  ⎭ Make | 100 μl | 100 μl | 100 μl |

*Freon 11 can be substituted.

Procedure

Micronize rac-[[2-[6-(4-acetyl-3-hydroxy-2-propylphenoxy)-hexyl]-3,4-dihydro-2-methyl-4-oxo-8-propyl-2-H-1-benzopyran-7-yl]oxy]acetic acid to the 1-10 micron particle range by air attrition and place in a appropriate container. Add glyceryl trioleate at room temperature. Chill the Freon to −30° C. and then add it to mixture. Seal a precise appropriate volumetric valve onto the container immediately after adding the Freon and place the container in an ultrasonic generator to disperse the rac-[[2-[6-(4-acetyl-3-hydroxy-2-propylphenoxy)hexyl]-3,4-dihydro-2-methyl-4-oxo-8-propyl-2H-1-benzopyran-7-yl]oxy]acetic acid in the Freon.

EXAMPLE 42

Aerosol Formulation (Sodium Salt Freon Suspension Aerosol)

| Ingredients | mg/100 μl | | |
|---|---|---|---|
| | 1 mg | 10 mg | 25 mg |
| rac-[[2-[6-(4-Acetyl-3-hydroxy-2-propylphenoxy)-hexyl]-3,4-dihydro-2-methyl-4-oxo-8-propyl-2H—1-benzopyran-7-yl]oxy]acetic acid sodium salt (micronized) | 1 mg | 10 mg | 25 mg |
| Oleic Acid | 0. 01 mg | 1.0 mg to | 3.0 mg |
| to | 0.03 mg | 3.0 mg | 7.5 mg |
| Freon 114* 30 Parts ⎫ To<br>Freon 12 70 Parts  ⎭ Make | 100 μl | 100 μl | 100 μl |

*Freon 11 can be substituted.

Procedure

Micronize the sodium salt of rac-[[2-[6-(4-acetyl-3-hydroxy-2-propylphenoxy)hexyl]-3,4-dihydro-2-methyl-4-oxo-8-propyl-2H-1-benzopyran-7-yl]oxy]acetic acid to the 1–10 micron particle range by air attrition and place in an appropriate container. Add glyceryl trioleate at room temperature. Chill the Freon to −30° C. and then add it to mixture. Seal a precise appropriate volumetric valve onto the container immediately after adding the Freon and place the container in an ultrasonic generator to disperse the sodium salt of rac-[[2-[6-(4-acetyl-3-hydroxy-2-propylphenoxy)hexyl]-3,4-dihydro-2-methyl-4-oxo-8-propyl-2H-1-benzopyran-7-yl]oxy]acetic acid in the Freon.

EXAMPLE 43

Aerosol Formulation (Freon Solution Aerosol)

| Ingredients | mg/100 μl | | |
|---|---|---|---|
| | 1.0 mg | 10.0 mg | 25.0 mg |
| rac-[[2-[6-(4-Acetyl-3-hydroxy-2-propylphenoxy)-hexyl]-3,4-dihydro-2-methyl-4-oxo-8-propyl-2H—1-benzopyran-7-yl]oxy]acetic acid (micronized) | 1.0 mg | 10.0 mg | 25.0 mg |
| Dimethylsulfoxide | 3.0 μl | 10.0 μl | 20.0 μl |
| Ethanol 99.9% | 6.0 μl | 6.0 μl | 6.0 μl |
| Methylene Chloride | 10 μl | 10 μl | 10 μl |
| Freon 12 To Make | 100 μl | 100 μl | 100 μl |

Procedure

Dissolve rac.-[[2-[6-(4-acetyl-3-hydroxy-2-propylphenoxy)-hexyl]-3,4-dihydro-2-methyl-4-oxo-8-propyl-2H-1-benzopyran-7-yl]oxy]-acetic acid in dimethylsulfoxide at room temperature in an appropriate container. Add the ethanol and methylene chloride to the mixture. Then add the Freon which has been chilled to −30° C. Seal a precise appropriate volumetric valve onto the container immediately after adding the Freon.

EXAMPLE 44

Aerosol Formulation (Freon Solution Aerosol)

| Ingredients | |
|---|---|
| rac-[[2-[6-(4-Acetyl-3-hydroxy-2-propylphenoxy)-hexyl]-3,4-dihydro-2-methyl-4-oxo-8-propyl-2H—1-benzopyran-7-yl]oxy]acetic acid (micronized) | 50.0 mg |
| Dimethylsulfoxide | 150 μl |
| Ethanol 99.9% | 0.3 ml |
| Methylene Chloride | 0.5 ml |
| Freon 12 | 4.2 ml |
| Total Volume | 5.0 ml |

Concentration of Active Ingredient 1 mg/0.1 ml

Procedure

The same procedure as in Example 43 was employed in this Example.

EXAMPLE 45

Nebulization Formulation (Solution for Nebulization)

| Ingredients | mg/ml | | |
|---|---|---|---|
| | 25.0 mg | 50.0 mg | 100.0 mg |
| rac-[[2-[6-(4-Acetyl-3-hydroxy-2-propylphenoxy)-hexyl]-3,4-dihydro-2-methyl-4-oxo-8-propyl-2H—1-benzopyran-7-yl]oxy]acetic acid (micronized) | 25.0 mg | 50.0 mg | 100.0 mg |
| Phosphate Buffer Containing Sodium Hydroxide to pH 7.8 To Make | 1.0 ml | 1.0 ml | 1.0 ml |

Procedure

Dissolve rac-[[2-[6-(4-acetyl-3-hydroxy-2-propylphenoxy)-hexyl]-3,4-dihydro-2-methyl-4-oxo-8-propyl-2H-1-benzopyran-7-yl]oxy]acetic acid into the phosphate buffer containing an equimolar amount of sodium hydroxide resulting in a solution having a pH of 7.8.

EXAMPLE 46

Capsule Formulation

| Ingredients | mg/capsule | | | |
|---|---|---|---|---|
| | 25 mg | 50 mg | 100 mg | 200 mg |
| rac-[[2-[4-(4-Acetyl-3-hydroxy-2-propyl-phenoxy)butyl]-3,4-dihydro-2-methyl-4-oxo-2H—1-benzopyran-7-yl]-acetic acid methyl ester | 25 | 50 | 100 | 200 |
| Lactose | 375 | 155 | 200 | 140 |
| Starch | 30 | 30 | 35 | 40 |
| Talc | 20 | 15 | 15 | 20 |
| Weight of capsule | 450 mg | 250 mg | 350 mg | 400 mg |

Procedure

Mill rac-[[2-[4-(4-Acetyl-3-hydroxy-2-propylphenoxy)butyl]-3,4-dihydro-2-methyl-4-oxo-2H-1-benzopyran-7-yl]oxy]acetic acid methyl ester, lactose and starch in a suitable mixer. Mill. Add talc and mix well. Encapsulate on suitable equipment.

EXAMPLE 47

Tablet Formulation (Wet granulation)

| Ingredients | mg/tablet | | | |
|---|---|---|---|---|
| | 25 mg | 50 mg | 100 mg | 200 mg |
| rac-[[2-[4-(4-Acetyl-3-hydroxy-2-propyl-phenoxy)butyl]-3,4-dihydro-2-methyl-4-oxo-2H—1-benzopyran-7-yl]-oxy]-acetic acid methyl ester | 25 | 50 | 100 | 200 |
| Lactose | 250 | 153 | 187 | 171 |
| Modified Starch | 55 | 25 | 35 | 45 |
| Pregelatinized Starch | 35 | 20 | 25 | 30 |
| Distilled water q.s. | — | — | — | — |
| Magnesium Stearate | 5 | 2 | 3 | 4 |
| Weight of tablet | 450 mg | 250 mg | 350 mg | 400 mg |

Procedure

Mix rac-[[2-[4-[(4-Acetyl-3-hydroxy-2-propylphenoxy)butyl]-3,4-dihydro-2-methyl-4-oxo-2H-1-benzopyran-7-yl]oxy]acetic acid methyl ester, lactose, modified starch and pregelatinized starch in a suitable mixer. Granulate with sufficient distilled water to proper consistency. Mill. Dry in a suitable oven. Mill and mix with magnesium stearate for 3 minutes. Compress on a suitable press equipped with appropriate punches.

EXAMPLE 48

Tablet Formulation (Direction Compression)

| Ingredients | mg/tablet 25 mg |
|---|---|
| rac-[[2-[4-(4-Acetyl-3-hydroxy-2-propylphenoxy)-butyl]-3,4-dihydro-2-methyl-4-oxo-2H—1-benzopyran-7-yl]oxy]-acetic acid methyl ester | 25 |
| Lactose | 181 |
| Avicel | 55 |
| Direct Compression Starch | 35 |
| Magnesium Stearate | 4 |
| Weight of tablet | 300 mg |

Procedure

Mill rac-[[2-[4-(4-Acetyl-3-hydroxy-2-propylphenoxy)butyl]-3,4-dihydro-2-methyl-4-oxo-2H-1-benzopyran-7-yl]oxy]acetic acid methyl ester with an equal amount of lactose. Mix well. Mix with avicel and direct compression starch, and the remaining amount of lactose. Mix well. Add magnesium stearate and mix for 3 minutes. Compression on a suitable press equipped with appropriate punches.

We claim:

1. A compound of the formula

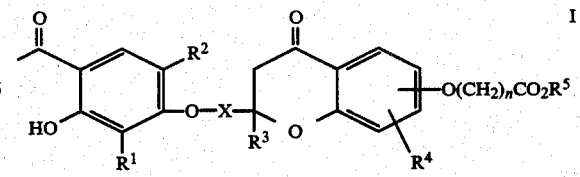

wherein $R^1$ is hydrogen or lower alkyl, $R^2$ is hydrogen or halogen, $R^3$ is hydrogen or lower alkyl, $R^4$ is hydrogen or lower alkyl, $R^5$ is hydrogen, lower alkyl or aralkyl, x is alkylene, and n is an integer from 1 to 6, an enantiomer thereof, or, when $R^5$ is hydrogen, a salt thereof with a pharmaceutically acceptable base.

2. A compound, in accordance with claim 1, wherein $R^5$ is hydrogen.

3. A compound, in accordance with claim 1, wherein $R^5$ is lower alkyl.

4. A compound, in accordance with claim 2, wherein $R^1$ is lower alkyl; $R^2$ is hydrogen; $R^3$ is lower alkyl; $R^4$ is lower alkyl; X is alkylene of 4 to 6 carbon atoms; and n is 1 to 4.

5. A compound, in accordance with claim 3, wherein $R^1$ is propyl; $R^2$ is hydrogen; $R^3$ is methyl; $R^4$ and $R^5$ are independently lower alkyl; X is alkylene of 4 to 6 carbon atoms; and n is 1 to 4.

6. A compound, in accordance with claim 2, wherein $R^1$ is lower alkyl; $R^2$ is hydrogen; $R^3$ is lower alkyl; $R^4$ is propyl; X is alkylene of 4 to 6 carbon atoms; and n is 1 to 4.

7. A compound, in accordance with claim 3, wherein $R^1$ is propyl; $R^2$ is hydrogen; $R^3$ is methyl; $R^4$ is propyl; $R^5$ is lower alkyl; X is alkylene of 4 to 6 carbon atoms; and n is 1 to 4.

8. A compound, in accordance with claim 1, rac-[[2-[6-(4-acetyl-3-hydroxy-2-propylphenoxy)hexyl]-3,4-dihydro-2-methyl-4-oxo-8-propyl-2H-1-benzopyran-7-yl]oxy]-acetic acid or its sodium salt.

9. A compound, in accordance with claim 1, rac-[[2-[4-(4-acetyl-3-hydroxy-2-propylphenoxy)butyl]-3,4-dihydro-2-methyl-4-oxo-2H-1-benzopyran-7-yl]oxy]acetic acid methyl ester.

10. A compound, in accordance with claim 1, rac-4-[[2-[4-(4-acetyl-3-hydroxy-2-propylphenoxy)butyl]-3,4-dihydro-2-methyl-4-oxo-8-propyl-2H-1-benzopyran-7-yl]oxy]butanoic acid ethyl ester.

11. A compound, in accordance with claim 1, rac-4-[[2-[4-(4-acetyl-3-hydroxy-2-propylphenoxy)butyl]-3,4-dihydro-2-methyl-4-oxo-8-propyl-2H-1-benzopyran-7-yl]oxy]butanoic acid.

12. A compound, in accordance with claim 1, rac-[[2-[4-(4-acetyl-3-hydroxy-2-propylphenoxy)butyl]-3,4-dihydro-2-methyl-4-oxo-8-propyl-2H-1-benzopyran-7-yl]oxy]acetic acid.

13. A pharmaceutical composition which comprises a compound of the formula

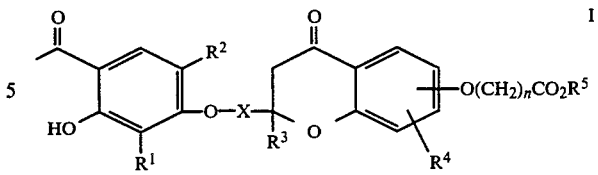

wherein $R^1$ is hydrogen or lower alkyl, $R^2$ is hydrogen or halogen, $R^3$ is hydrogen or lower alkyl, $R^4$ is hydrogen or lower alkyl, $R^5$ is hydrogen, lower alkyl or aralkyl, X is alkylene and n is an integer from 1 to 6, an enantiometer thereof, or, when $R^5$ is hydrogen, a salt thereof with a pharmaceutically acceptable base, and an inert carrier material.

14. A pharmaceutical composition, in accordance with claim 13, wherein the compound is rac-[[2-[6-(4-acetyl-3-hydroxy-2-propylphenoxy)hexyl]-3,4-dihydro-2-methyl-4-oxo-8-propyl2H-1-benzopyran-7-yl]oxy]-acetic acid.

15. A pharmaceutical composition, in accordance with claim 13, wherein the compound in rac.-[[2-[4-(4-acetyl-3-hydroxy-2-propylphenoxy)butyl]-3,4-dihydro-2-methyl-4oxo2H-1-benzopyran-7-yl]oxy]acetic acid methyl ester.

16. A method of treating leukotriene induced allergic conditions which comprises administering to a host requiring such treatment an effective amount of a compound of the formula

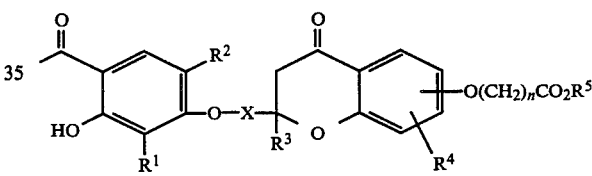

wherein $R^1$ is hydrogen or lower alkyl, $R^2$ is hydrogen or halogen, $R^3$ is hydrogen or lower alkyl, $R^4$ is hydrogen or lower alkyl, $R^5$ is hydrogen, lower alkyl or aralkyl, X is alkylene and n is an integer from 1 to 6, an enantiomer thereof, or, when $R^5$ is hydrogen, a salt thereof with a pharmaceutically acceptable base.

17. A method, in accordance with claim 16, wherein the compound is rac-[[2-[6-(4-acetyl-3-hydroxy-2-propylphenoxy)hexyl]-3,4-dihydro-2-methyl-4-oxo-8-propyl-2H-1-benzopyran-7-yl]oxy]-acetic acid.

18. A method, in accordance with claim 16, wherein the compound is rac-[[2-[4-(4-acetyl-3-hydroxy-2-propylphenoxy)butyl]-3,4-dihydro-2-methyl-4-oxo-2H-1-benzopyran-7yl]oxy]acetic acid methyl ester.

* * * * *